(12) United States Patent
Goode et al.

(10) Patent No.: US 8,152,791 B2
(45) Date of Patent: Apr. 10, 2012

(54) CATHETER LOCKING MECHANISM

(75) Inventors: Louis B. Goode, Cranberry Township, PA (US); Peter John Morcheid, Spring Church, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/270,268

(22) Filed: Nov. 13, 2008

(65) Prior Publication Data

US 2010/0121313 A1 May 13, 2010

(51) Int. Cl.
*A61M 25/16* (2006.01)

(52) U.S. Cl. ...................................................... 604/535

(58) Field of Classification Search .......... 604/533–539, 604/288.01–288.04
See application file for complete search history.

(56) References Cited

U.S. PATENT DOCUMENTS

| 5,312,337 | A | * | 5/1994 | Flaherty et al. | 285/278 |
| 5,549,583 | A | * | 8/1996 | Sanford et al. | 604/535 |
| 5,637,102 | A | | 6/1997 | Tolkoff et al. | 604/283 |
| 2006/0264911 | A1 | | 11/2006 | Nelson | 604/890.1 |

FOREIGN PATENT DOCUMENTS

| EP | 0343910 A2 | 11/1989 |
| WO | WO 92/07215 A1 | 4/1992 |

* cited by examiner

*Primary Examiner* — Kevin C Sirmons
*Assistant Examiner* — Kami A Bosworth
(74) *Attorney, Agent, or Firm* — Brinks Hofer Gilson & Lione

(57) ABSTRACT

A locking mechanism for maintaining a position of a catheter on a beaded connector tube of an implantable device. A first lock member has a plurality of slots formed along its outer surface. A second lock member is dimensioned such that at least a slotted portion of the first member is receivable in an axial passageway of the second member. The second member has a plurality of tabs extending into the axial passageway wherein a tab is receivable in a respective slot to form a locking connection between the lock members. The lock members are aligned upon formation of the locking connection wherein the connector tube and catheter are receivable along the respective axial passageways, and the beaded connector tube portion is disposed on an opposite side of the tabs from the implantable device.

16 Claims, 5 Drawing Sheets

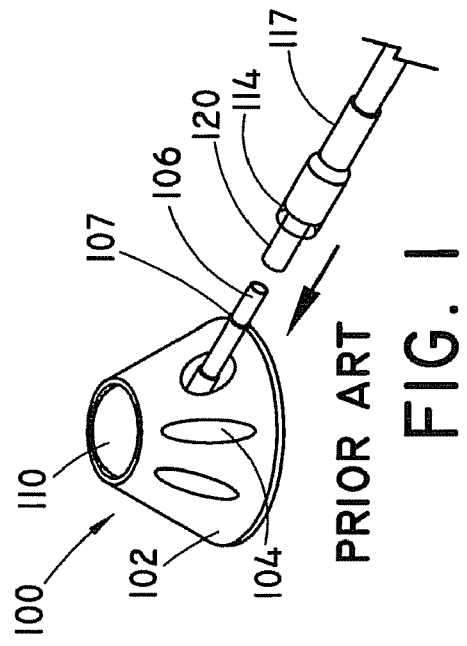
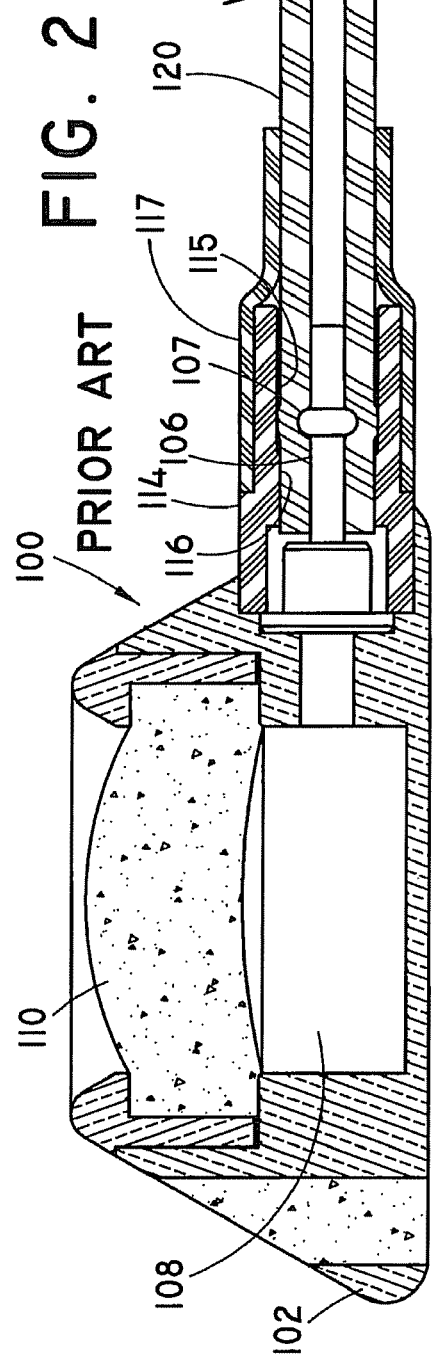
FIG. 1 PRIOR ART
FIG. 2 PRIOR ART

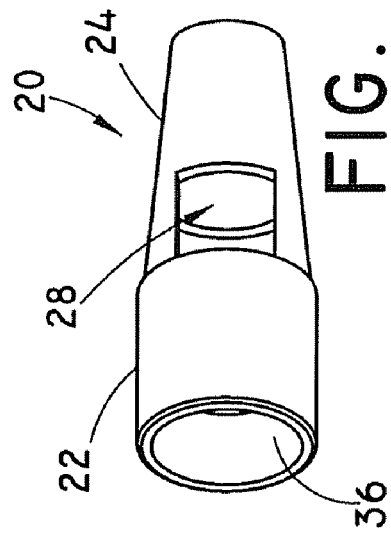
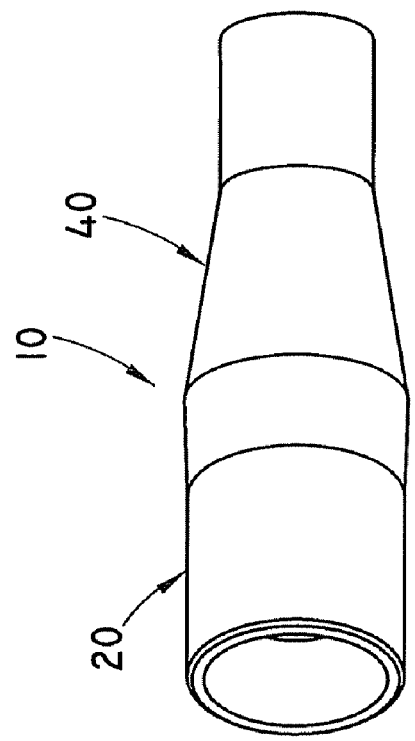
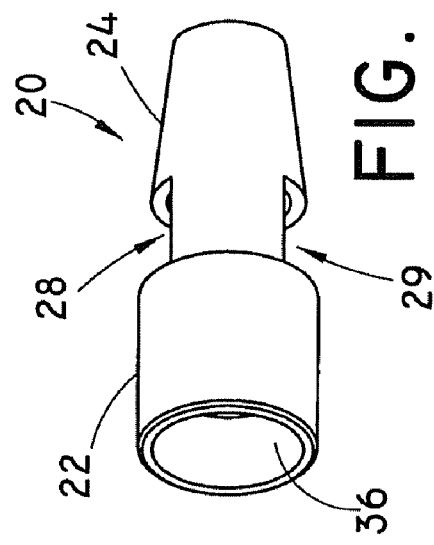
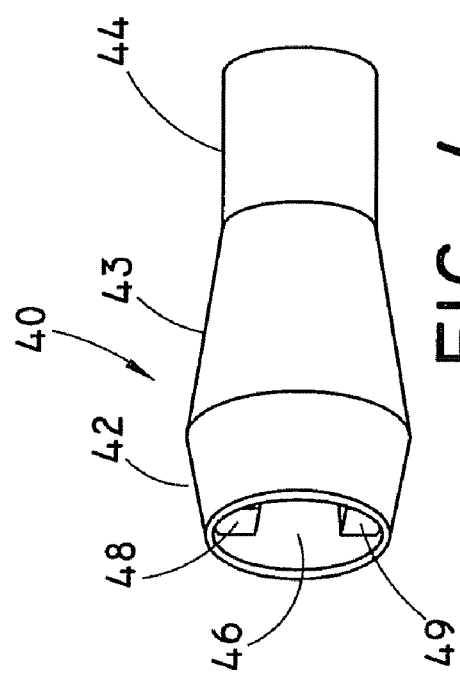

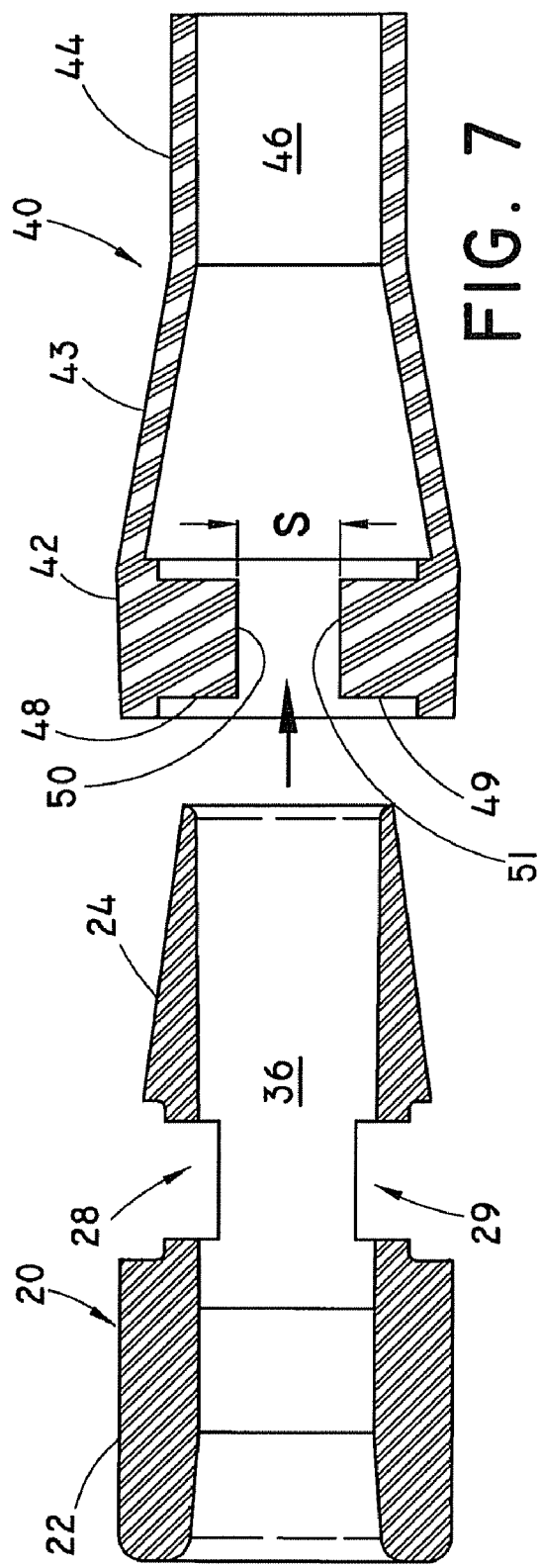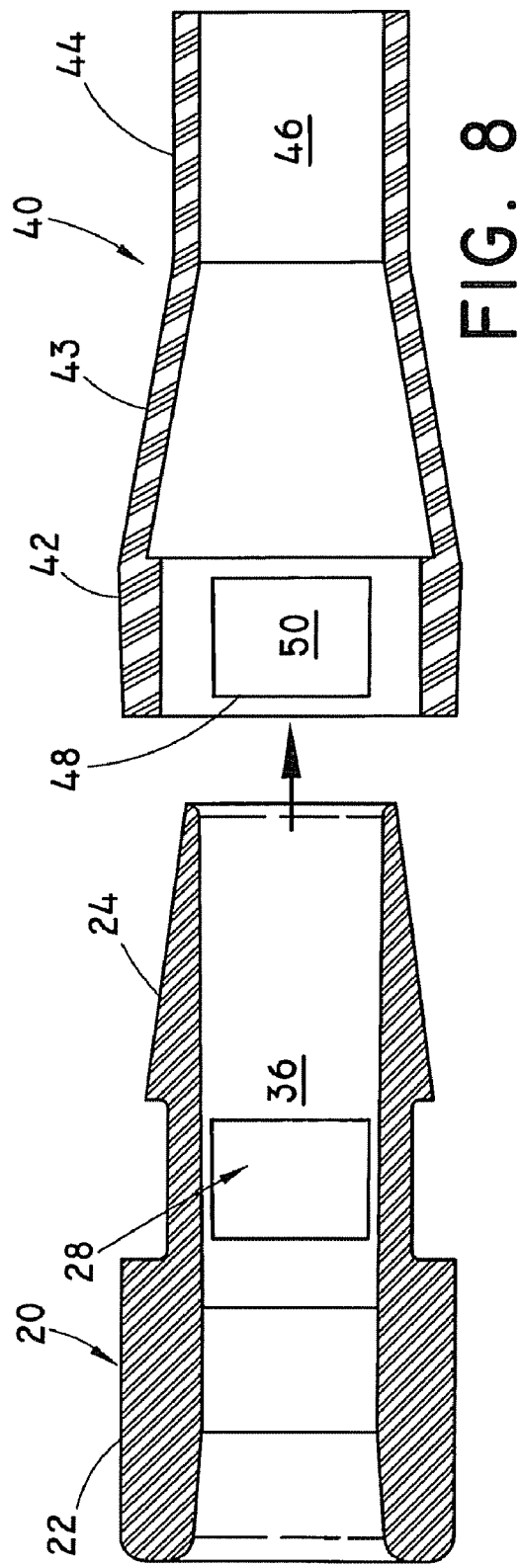

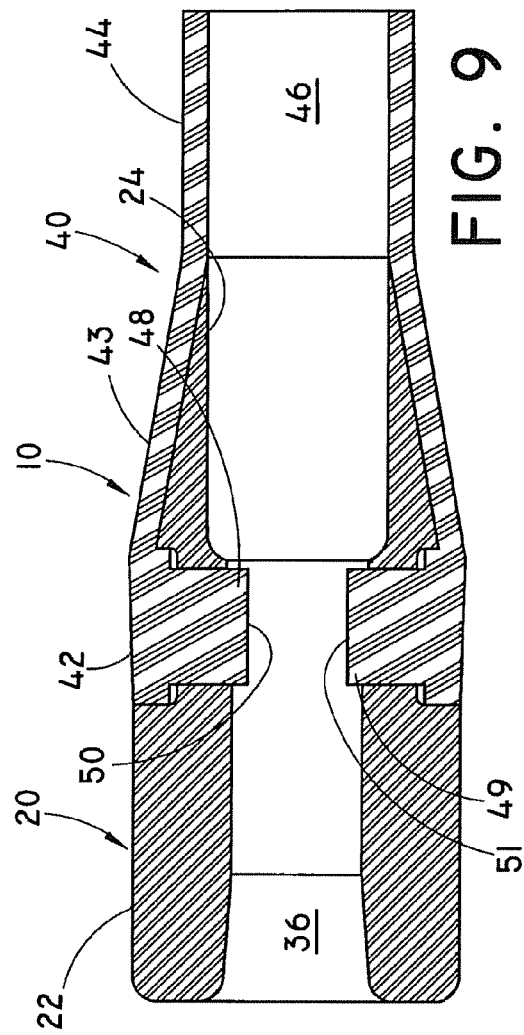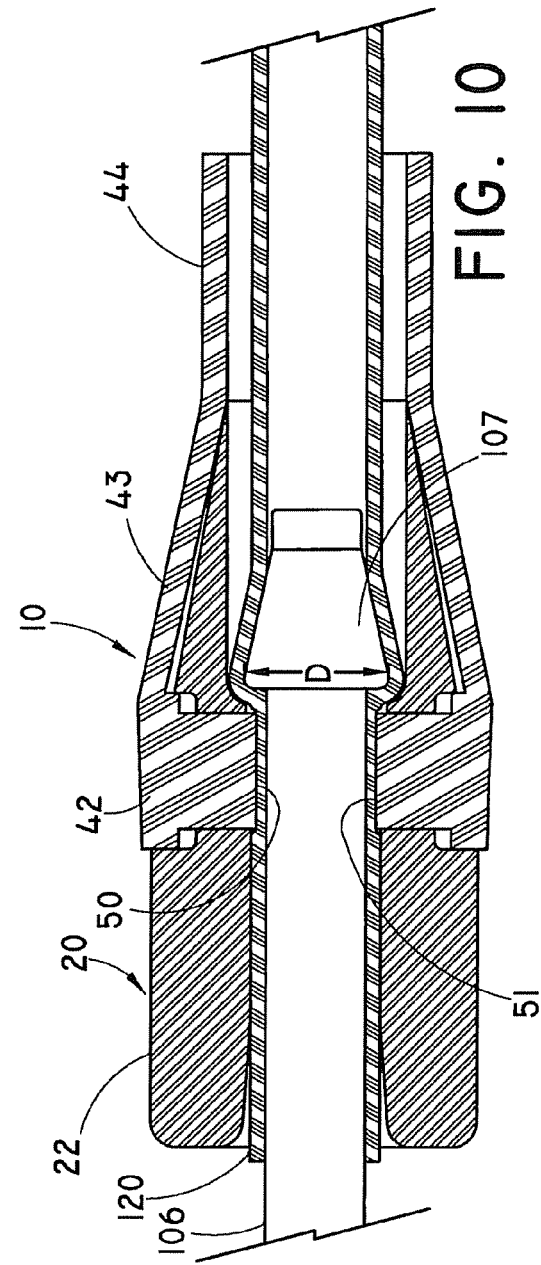

CATHETER LOCKING MECHANISM

BACKGROUND

1. Technical Field

The present invention relates to an apparatus for securing a connection between two medical structures implanted in the body of a patient, and more particularly, to a locking mechanism for locking an end of a catheter onto the connector tube of an implantable vascular access device.

2. Background Information

Vascular access systems are utilized in the medical field for the transmission of fluids between a reservoir in an implanted vascular access device, and a body vessel in the patient. The vascular access device is surgically implanted by a physician into the subcutaneous tissue of a patient. Frequently, the device is implanted in the clavicular area of the chest, although it may also be implanted in other areas having sufficient underlying bony structure to provide support for the device. A catheter extends between the connector tube of the vascular access device and the body vessel, such as a blood vessel, for establishing fluid communication therebetween. The fluid generally comprises a liquid medicament that is injected into a reservoir of the vascular access device for use in treating a medical condition of the patient. Alternatively, the fluid can comprise a body fluid that is collected in the reservoir of the vascular access device for withdrawal and analysis.

Typically, a vascular access device is implanted in a patient in situations in which it is expected that treatment of the patient with the medicament will continue for at least a period of several months. One of the most common uses of such devices is for cancer treatment, where a chemotherapeutic agent is injected into the reservoir, and transported therefrom through the catheter and vessel to a targeted body site.

A vascular access device typically includes a septum or similar penetrable closure through which the liquid medicament may be injected or otherwise transferred from the outside environment into the reservoir. When the device includes a septum, the septum generally comprises an elastomeric wall that covers all or a part of a surface of the device that is accessible to a needle. The septum is penetrated by the needle for injecting the medicament into the reservoir, or alternatively, for withdrawing blood or other body fluid from the reservoir.

A vascular access device is implanted into a pocket area of the subcutaneous tissue that has been deemed suitable for such use by the physician. The device is implanted in a manner such that the septum is readily accessible to the needle, so that the needle injection can be accomplished without undue complication and trauma to the patient. Once implanted, the device remains generally stationary in the pocket so that needle access to the device is not compromised. In many cases, the device is sutured or otherwise attached to available tissue in the body pocket to inhibit exceptional movement or shifting.

In a typical vascular access device, the connector tube of the implanted vascular access device is typically connected to a catheter by pushing the catheter over the connector tube. Thereafter, a rigid sleeve, typically fabricated from plastic or metal, is pushed over the catheter and the connector tube to maintain the catheter in position relative to the tube. This design has certain shortcomings. For example, during insertion of the sleeve over the catheter, the catheter is highly compressed between the minor diameter of the sleeve and the bead of the connector tube. The catheter then re-expands after the minor diameter has gone past the bead. The minor diameter creates a step which is employed to insure that the sleeve will not subsequently inadvertently withdraw from the connection. Since the only elasticity in this connection is in the compression of the catheter, the physician may have difficulty "feeling" that the connection has been properly effected. In addition, the high residual stresses created in the catheter render it susceptible to stress cracking over time. Further discussion of these deficiencies is provided in the description of the prior art designs illustrated in FIGS. 1 and 2 herein.

It would be desirable to provide a locking mechanism for a vascular access device that provides for secure attachment between the connector tube and the catheter, and that avoids the shortcomings of the prior art.

SUMMARY

The present invention addresses the problems of the prior art. In one form thereof, the invention comprises a locking mechanism for maintaining a position of a catheter on a beaded connector tube of an implantable vascular access device. The locking mechanism includes first and second lock members. The first lock member comprises an elongated body having an outer surface, and having an axial passageway extending therethrough. The first lock member further has a plurality of slots formed along its outer surface. The second lock member comprises an elongated body having an outer surface and an inner surface, and having an axial passageway extending therethrough. The second lock member is dimensioned such that at least a portion of the outer surface of the first lock member having the slots formed therealong is receivable in the second lock member axial passageway. The second lock member has a plurality of tabs extending radially into the axial passageway from the inner surface. The tabs are sized and arranged along the inner surface such that a tab is receivable in a respective slot to form a locking connection between the first and second lock members when the first lock member outer surface portion is received in the second lock member axial passageway. The first and second lock members are alignable upon formation of the locking connection such that the connector tube and catheter positioned thereon are receivable along the first and second lock member axial passageways, and the beaded portion of the connector tube is disposed on an opposite side of the tabs from the vascular access device.

In another form thereof, the invention comprises a medical assembly for implantation in a patient. The medical assembly includes a vascular access device comprising a body portion having a fluid reservoir therein, and a connector tube for conveyance of a fluid between the reservoir and a vessel of a patient. At least a portion of the connector tube extends outwardly from the body portion and includes a large diameter segment along a portion of its length. A catheter has first and second ends, and is sized such that the first end is receivable over the large diameter segment of the connector tube, and the second end is extendable into the vessel for conveyance of the fluid. A locking mechanism is provided for maintaining a position of the catheter first end over the large diameter segment of the connector tube. The locking mechanism comprises a first lock member and a second lock member. The first lock member comprises an elongated body having an outer surface and having an axial passageway extending therethrough. The outer surface has at least one slot formed therealong. The axial passageway of the first lock member is dimensioned such that the connector tube with the catheter received thereover is receivable therethrough and the beaded portion of the connector tube is axially extendable in the passageway beyond the slot. The second lock member comprises an elongated body having an outer surface and an inner surface, and having an axial passageway extending therethrough. The second lock member is dimensioned such that at least a portion of the outer surface of the first lock member having the slot formed therealong is receivable in the second lock member axial passageway. The second lock member has at least one tab extending radially into the second lock member axial passageway from the inner surface. The tab is sized and shaped to fit into the slot to form a locking connection between the first and second lock members, and to inhibit disengagement of the connector tube and the catheter.

In still another form thereof, the invention comprises a method for locking a catheter onto a connector tube of an implantable vascular access device, wherein the connector tube has a large diameter portion along its length. A locking mechanism comprising a first lock member and a second lock member is provided. The first lock member comprises an elongated body having an outer surface and an axial passageway extending therethrough, and having a plurality of slots formed along the outer surface. The second lock member comprises an elongated body having an outer surface and an inner surface, and an axial passageway extending therethrough. The second lock member is dimensioned such that at least a portion of the outer surface of the first lock member having slots formed therealong is receivable in the second lock member axial passageway. The second lock member has a plurality of tabs extending radially into the axial passageway from the inner surface. The tabs are sized and arranged along the inner surface such that a tab is receivable in a respective slot to form a locking connection between the first and second lock members when the first lock member outer surface portion is received in the second lock member axial passageway. At least a pair of tabs have respective tab ends separated by a spacing, wherein the spacing is than the large diameter. The catheter is slid along the connector tube such that an end of the catheter extends over and beyond the large diameter portion. The locking mechanism is positioned over the catheter and the connector tube such that the tabs extend beyond the large diameter portion, thereby inhibiting withdrawal of the connector tube and disengagement of the catheter from the connector tube.

BRIEF DESCRIPTION OF THE DRAWINGS

FIG. 1 is a perspective view of a prior art vascular access device and catheter;

FIG. 2 is a cross-sectional view of the prior art vascular access device shown in FIG. 1, illustrating a rigid sleeve positioned over the catheter to maintain the position of the catheter over the device connector tube;

FIG. 3 is a side view of a first lock member for use in a locking mechanism according to an embodiment of the present invention;

FIG. 3A is another side view of the lock member, rotated 90° from the orientation of FIG. 3;

FIG. 4 is a side view of a second lock member for engagement with the lock member of FIG. 3;

FIG. 5 is a side view of a locking mechanism formed by engaging the first and second lock members of FIGS. 3 and 4;

FIG. 7 is a cross-sectional view of the first and second lock members arranged as in FIG. 6;

FIG. 8 is a cross-sectional view of the first and second lock members, rotated 90° from the orientation shown in FIG. 7;

FIG. 9 is a cross-sectional view of the first and second lock members arranged to form a locking mechanism according to an embodiment of the present invention; and FIG. 10 is a cross-sectional view of the locking mechanism as shown in FIG. 9 in locking arrangement with a catheter and the beaded connector tube.

DETAILED DESCRIPTION OF THE DRAWINGS AND THE PRESENTLY PREFERRED EMBODIMENTS

Figure 6:
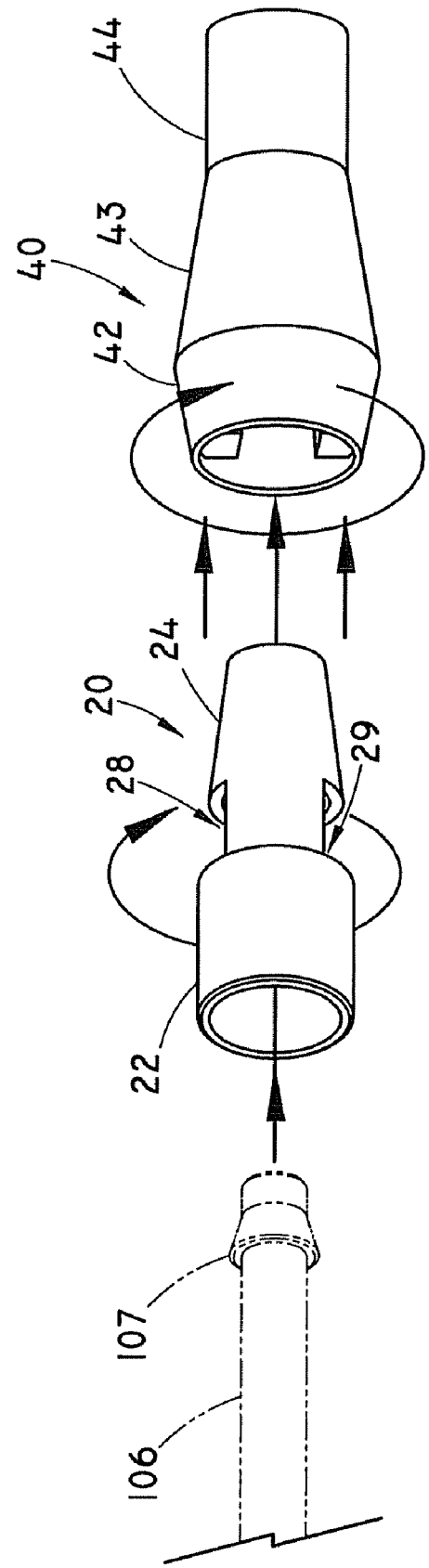
FIG. 6 is a view of the first and second lock members arranged prior to forming the locking mechanism of the present invention, also illustrating in phantom a beaded connector tube of a vascular access device.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 is a perspective view of a conventional vascular access device 100 of the type that is well known in the art. Also illustrated in FIG. 1 is a conventional catheter 120 situated for placement over connector tube 106 of vascular access device 100 in well-known fashion. FIG. 2 illustrates a cross-sectional view of the conventional vascular access device 100 of FIG. 1, wherein the catheter 120 has been inserted over connector tube 106 to establish fluid communication between a body vessel and a fluid reservoir 108 disposed interiorly of vascular access device 100.

Conventional vascular access device 100 includes an outer main body portion 102 formed of a biocompatible material, such as a metal (e.g. titanium) or relatively rigid stiff polymeric material (e.g. polysulfone). Body portion 102 may be formed to include one or more suture holes 104 through which the physician may thread a suture to ligate the vascular access device to body tissue. A septum 110 is provided along an upper surface of vascular access device 100. Septum 110 generally comprises an elastomeric wall that is penetrable by a needle (not shown) to provide access to fluid reservoir 108. One example of a conventional vascular access device 100 is the VITAL-PORT® device, available from Cook Incorporated, of Bloomington, Ind.

As shown in FIG. 2, a generally rigid tubular sleeve 114 is fitted over catheter 120 to inhibit disengagement of the catheter from the connector tube. In the version shown, sleeve 114 acts as a locking mechanism to prevent such disengagement. The locking mechanism may also include an outer silicone sleeve 117 that is press-fit over sleeve 114. Vascular access devices are well known in the medical arts, and the vascular access device 100 illustrated and described herein is merely one example of such devices. The invention described herein may be utilized in connection with any such devices, provided that the device includes a connector tube similar to that described herein.

In the prior art device shown, catheter 120 is engaged with vascular access device connector tube 106 by first pushing the catheter over the exposed end of the connector tube. Sleeve 114 is thereafter inserted over the catheter and the tube, by pushing the sleeve in the direction of the arrow in FIG. 1. Sleeve 114 is typically formed of a rigid plastic or metal, and has a major inner diameter 115 and a minor inner diameter 116. Minor inner diameter 116 is provided at the leading edge of the sleeve, and, as shown in FIG. 2, defines a step which inhibits inadvertent withdrawal of sleeve 114 from the connection. As sleeve 114 passes over catheter 120, the portion of the catheter positioned directly over a larger-diameter beaded portion 107 of the connector tube becomes highly compressed when minor diameter 116 of rigid sleeve 114 passes over the bead. After minor inner diameter 116 clears this portion of the catheter, the catheter portion re-expands to its normal diameter. Since the only elasticity in this connection is in the compression of the catheter, the physician may have difficulty determining that the connection has been properly effected. In addition, the high residual stresses in the catheter, most notably in the highly compressed catheter portion described above, render it susceptible to stress cracking over time.

FIG. 3 illustrates a side view of a first lock member 20 of a locking mechanism 10 (FIG. 5) of the present invention. FIG. 3A illustrates another side view of first lock member 20, rotated 90° from the orientation of FIG. 3. FIG. 4 illustrates a side view of a second lock member 40. FIG. 5 is a side view of a locking mechanism 10 according to an embodiment of the present invention, formed by engaging the first and second lock members shown in respective FIGS. 3 and 4, in a manner to be further described herein.

In the embodiment shown, lock member 20 comprises a generally rigid elongated structure having a generally cylindrical portion 22 at one axial end, and a gently tapered portion 24 at the other axial end. A passageway 36 extends axially through lock member 20. Opposing slots 28, 29 are formed along each side of lock member 20. In the embodiment shown, slots 28, 29 are formed as respective radial depressions along the outer surface of lock member 20; however, any slotted structure along the surface of lock member 20 that is capable of receiving a tab as described herein may be substituted for the configuration shown. Preferably, slots 28, 29 open into the interior passageway 36 of lock member 20.

Lock member 20 is preferably formed, e.g., by molding or machining, from a relatively rigid composition such as a metal (e.g., titanium), a metal alloy (e.g., stainless steel), or a rigid polymer (e.g., acetyl or polysulfone). Preferably, lock member 20 is formed from a relatively high durometer material, e.g., a material having a durometer between about 65 and 80 (Shore D).

FIG. 4 illustrates a side view of a second lock member 40 of the locking mechanism of the present invention. In the embodiment shown, second lock member 40 has a larger diameter portion 42 and a smaller diameter portion 44. A transition 43 interconnects larger diameter portion 42 and smaller diameter portion 44. A passageway 46 extends axially through second lock member 40. Preferably, at least the inner diameter of passageway 46 tapers to mate with the tapered outer diameter of lock member 20. Additionally, this inner diameter may also be sized to mate with a catheter (to be described) to provide strain relief on the catheter during catheter bending. A pair of opposing tabs 48, 49 extend radially into passageway 46. Tabs 48, 49 are sized and shaped to fit within respective slots 28, 29 of first lock member 20.

Lock member 40 may be formed, e.g., molded or machined, from a relatively rigid polymer or metal, or more preferably, from a dual durometer material, such as silicone. When formed from a dual durometer material, lock member 40 may have an outer shell of a relatively high durometer. An inner shell (including tabs 48, 49) may have a more flexible durometer, e.g. about 50. In this way, the tabs have sufficient flexibility such that they may be readily advanced into slots 28, 29. By providing an outer shell of a higher durometer, a positive resistance may be provided against an inadvertent needle stick, and against inadvertent mechanical pull-out.

FIG. 6 is a side view illustrating the alignment of first lock member 20 and second lock member 40 prior to engagement for forming locking mechanism 10. For perspective, a vascular access device connector tube 106 is shown in phantom. Connector tube 106 includes a conventional larger-diameter portion, shown here as beaded portion 107. As indicated above, connector tubes of this type are well-known in the art.

FIG. 7 is a cross-sectional view of the first and second lock members 20, 40 arranged as in FIG. 6. As illustrated, tabs 48, 49 have respective radial ends 50, 51. In a preferred embodiment, ends 50, 51 are separated by a space S. FIG. 8 is a cross-sectional view of first and second lock members 20, 40, rotated 90° from the orientation shown in FIG. 7.

FIG. 9 is a cross-sectional view illustrating the engagement of respective first and second lock members 20, 40 to form a locking mechanism 10, according to an embodiment of the present invention. As illustrated, tabs 48, 49 of lock member 40 are received in respective slots 28, 29 of lock member 20.

FIG. 10 is a cross-sectional view of the locking mechanism 10 defined by defined by lock members 20, 40. Locking mechanism 10 is illustrated in locking arrangement with a catheter 120 and beaded connector tube 106. Catheter 120 and beaded connector tube 106 are conventional, and the reference numerals from the prior art structures of FIGS. 1 and 2 have been retained to designate these conventional elements. In this figure, catheter 120 is engaged with vascular access device connector tube 106 by first pushing the catheter over the exposed end of the connector tube, as further explained above with reference to FIGS. 1 and 2.

Lock member 20 may then be slid over catheter 120 such that opposing slots 28, 29 extend beyond larger diameter beaded portion 107 of the connector tube. Lock member 40 may then be slid over tapered portion 24 of lock member 20 until flexible tabs 48, 49 are received in respective slots 28, 29. As a further alternative, lock members 20 and 40 may be engaged to form locking mechanism 10 prior to sliding the locking mechanism over connector tube beaded portion 107. In either alternative, once the locking mechanism 10 is securely in position, the mechanism will be aligned with the catheter and connector tube as illustrated in FIG. 10.

For optimal results, it is preferred to size and align the tabs 48, 49 of lock member 40 such that spacing S between respective tab ends 50, 51 (FIG. 7), is less the maximum diameter D of beaded portion 107. (FIG. 10). As a result, the radially inward extension of tab ends 50, 51, inhibits withdrawal of connector tube beaded portion 107 in the direction of the vascular access device, and eventual disengagement of the connector tube from the catheter.

It is therefore intended that the foregoing detailed description be regarded as illustrative rather than limiting, and that it be understood that it is the following claims, including all equivalents, that are intended to define the spirit and scope of this invention.

The invention claimed is:

1. A medical assembly for implantation in a patient, comprising:
   a vascular access device, the vascular access device comprising a body portion having a fluid reservoir therein, and a connector tube for conveyance of a fluid between the reservoir and a vessel of a patient, said connector tube having a length, wherein a first segment of said length extends outwardly from said body portion to a second segment, said second segment having a greater diameter than said first segment;
   a catheter having first and second ends, said catheter sized such that said first end is receivable over said second segment of said connector tube onto said first segment, and said second end is extendable into said vessel for conveyance of said fluid; and a locking mechanism structured for maintaining a position of said catheter first end on said first segment of said connector tube, said locking mechanism comprising a first lock member and a second lock member, said first lock member comprising an elongated body having an outer surface and having an axial passageway extending therethrough, said outer surface having at least one slot formed therealong, said axial passageway of said first lock member dimensioned such that said connector tube with said catheter received thereover is receivable therethrough and said second segment of said connector tube is axially extendable in said passageway beyond said slot; said second lock member comprising an elongated body having an outer surface and an inner surface, and having an axial passageway extending therethrough, said second lock member dimensioned such that at least a portion of said outer surface of said first lock member having said at least one slot formed therealong is receivable in said second lock member axial passageway, said second lock member having at least one tab extending radially into said second lock member axial passageway from said inner surface, said at least one tab sized and shaped to fit into said at least one slot to form a locking connection between said first and second lock members, and for inhibiting a disengagement of said connector tube and said catheter.

2. The medical assembly of claim 1, wherein said first lock member comprises two slots, and said second lock member comprises two tabs, said tabs positioned at diametrically opposite sides of said inner surface of said second lock member.

3. The medical assembly of claim 2, wherein said tabs are aligned such that a distance between said tab end portions when said first and second lock members are in said locking connection is less than a diameter of said second segment of said connector tube.

4. The medical assembly of claim 1, wherein said first lock member comprises at least two slots along said outer surface, and said second lock member comprises at least two tabs extending radially into said axial passageway, each of said tabs sized and shaped to fit into a separate one of said slots to form said locking connection, each of said tabs having an end portion, said tabs aligned such that a distance between said tab end portions is less than a diameter of said second segment of said connector tube.

5. The medical assembly of claim 1, wherein said first lock member comprises at least two slots along said outer surface, and said second lock member comprises at least two tabs extending radially into said axial passageway, each of said tabs sized and shaped to fit into a separate one of said slots to form said locking connection, each of said tabs having an end portion, said tabs aligned such that a distance between opposing tab end portions is less than a diameter of said connector tube maximal diameter segment.

6. The medical assembly of claim 5, wherein said slots extend through said first lock member elongated body to said first lock member axial passageway, and wherein a distal tip of said respective tabs extend into said first lock member axial passageway when said first and second lock members are in said locking connection.

7. The medical assembly of claim 5, wherein said first lock member comprises a generally cylindrical outer portion at one axial end thereof and a tapered outer portion at the other axial end.

8. The medical assembly of claim 7, wherein said second lock member axial passageway has a tapered portion dimensioned to receive the tapered portion of said first lock member.

9. The medical assembly of claim 8, wherein said first lock member comprises a generally rigid composition, and at least said tab members of said second lock member comprise a generally flexible composition.

10. The medical assembly of claim 9, wherein said first lock member comprises a metal, a metal alloy, or a rigid polymer, and said second lock member comprises silicone.

11. A method of locking a catheter on a connector tube of an implantable vascular access device, said vascular access device including a body portion having a fluid reservoir therein, and a connector tube extending from said body portion for conveying a fluid from said reservoir to a vessel of a patient, said connector tube having a length, wherein a first segment of said length extends outwardly from said body portion and a second segment of said length extends distal of said first segment, said second segment having a greater diameter than said first segment, comprising:
providing a locking mechanism comprising a first lock member and a second lock member, said first lock member comprising an elongated body having an outer surface and having an axial passageway extending therethrough, and having a plurality of slots formed along said outer surface; said second lock member comprising an elongated body having an outer surface and an inner surface, and having an axial passageway extending therethrough, said second lock member dimensioned such that at least a portion of said outer surface of said first lock member having said slots formed therealong is receivable in said second lock member axial passageway, said second lock member having a plurality of tabs extending radially into said axial passageway from said inner surface, said tabs sized and arranged along said inner surface such that a tab is receivable in a respective one of said plurality of slots to form a locking connection between said first and second lock members when said first lock member outer surface portion is received in said second lock member axial passageway, at least a pair of said tabs having tab ends separated by a spacing, said spacing being less than said diameter of said second segment;
sliding said catheter along said connector tube such that an end of said catheter extends over said second segment onto said first segment of said connector tube; and
positioning said locking mechanism over said catheter and said connector tube second segment such that said tabs extend over said first segment, thereby inhibiting withdrawal of said connector tube and disengagement of said catheter end from said connector tube.

12. The method of claim 11, wherein said locking mechanism is positioned over said catheter and said connector tube by first positioning said first lock member over said catheter and connector tube, and then positioning said second lock member with said first lock member to form said locking connection.

13. The method of claim 11, wherein said first lock member comprises a generally cylindrical outer portion at one axial end thereof and a tapered outer portion at the other axial end, and said second lock member axial passageway has a tapered portion dimensioned to receive the tapered portion of said first lock member.

14. The method of claim 11, wherein said first lock member comprises a generally rigid composition, and at least said tab members of said second lock member comprise a generally flexible composition.

15. The method of claim 14, wherein said first lock member comprises a metal, a metal alloy, or a rigid polymer, and said second lock member comprises silicone.

16. A medical assembly for implantation into a patient, comprising:

a vascular access device, the vascular access device comprising a body portion having a fluid reservoir therein, and comprising a connector tube for conveyance of a fluid between the reservoir and a vessel of a patient, said connector tube having a length, a first segment of said length extending outwardly from said body portion to a second segment, and a third segment of said length extending beyond said second segment, said second segment having a greater diameter than a diameter of said first segment and said third segment;

a catheter having first and second ends, the catheter sized such that said catheter first end is receivable over the second and third segments of the connector tube onto the first segment, and said catheter second end is extendable into said vessel for conveyance of said fluid; and a locking mechanism for maintaining a position of said catheter first end over the second and third segments of said connector tube and onto said first segment, the locking mechanism comprising a first lock member and a second lock member, said first lock member comprising an elongated body having an outer surface and having an axial passageway extending therethrough, said outer surface having a pair of slots formed therealong, said axial passageway of said first lock member dimensioned such that said connector tube with said catheter received thereover is receivable therethrough and said second segment of said connector tube is axially extendable in said passageway beyond said slots; said second lock member comprising an elongated body having an outer surface and an inner surface, and having an axial passageway extending therethrough, said second lock member dimensioned such that at least a portion of said outer surface of said first lock member having said slots formed therealong is receivable in said second lock member axial passageway, said second lock member having a pair of tabs, said tabs having end portions extending radially into said second lock member axial passageway from said inner surface and disposed at diametrically opposite sides of the inner surface of the second lock member, a respective tab sized and shaped to fit into each one of said slots to form a locking connection between said first and second lock members, said tabs being aligned and dimensioned such that a distance between said tab end portions when said first and second lock members are in said locking connection is less than a diameter of said connector tube second segment, said locking connection positioned intermediate said second segment and said body portion along the length of the connector tube first segment for inhibiting a disengagement of said connector tube and said catheter.

* * * * *